United States Patent
Childers

(10) Patent No.: US 7,926,486 B2
(45) Date of Patent: *Apr. 19, 2011

(54) PARAMETER OPTIMIZATION IN SLEEP APNEA TREATMENT APPARATUS

(76) Inventor: Winthrop D. Childers, San Diego, CA (US)

( * ) Notice: Subject to any disclaimer, the term of this patent is extended or adjusted under 35 U.S.C. 154(b) by 122 days.

This patent is subject to a terminal disclaimer.

(21) Appl. No.: 12/390,489

(22) Filed: Feb. 22, 2009

(65) Prior Publication Data

US 2009/0151725 A1 Jun. 18, 2009

Related U.S. Application Data

(63) Continuation of application No. 12/271,927, filed on Nov. 16, 2008, which is a continuation of application No. 11/224,548, filed on Sep. 12, 2005, now Pat. No. 7,469,698.

(60) Provisional application No. 60/609,897, filed on Sep. 14, 2004.

(51) Int. Cl.
*A61M 11/00* (2006.01)

(52) U.S. Cl. .......... 128/204.23; 128/204.18; 128/204.21

(58) Field of Classification Search ............. 128/204.21, 128/204.23, 204.18
See application file for complete search history.

(56) References Cited

U.S. PATENT DOCUMENTS

| | | | |
|---|---|---|---|
| 5,492,113 A | 2/1996 | Estes et al. | |
| 6,041,780 A | 3/2000 | Richard et al. | |
| 6,223,064 B1 | 4/2001 | Lynn et al. | |
| 6,398,739 B1 | 6/2002 | Sullivan et al. | |
| 6,427,689 B1 | 8/2002 | Estes et al. | |
| 6,502,572 B1 | 1/2003 | Berthon-Jones et al. | |
| 6,526,974 B1 | 3/2003 | Brydon et al. | |
| 6,550,478 B2 | 4/2003 | Remmers et al. | |
| 6,564,797 B1 | 5/2003 | Mechlenburg et al. | |
| 6,591,834 B1 | 7/2003 | Colla et al. | |
| 6,629,527 B1 | 10/2003 | Estes et al. | |
| 6,635,021 B1 | 10/2003 | Sullivan et al. | |
| 6,666,830 B1 | 12/2003 | Lehman et al. | |
| 6,675,797 B1 | 1/2004 | Berthon-Jones | |
| 6,705,315 B2 | 3/2004 | Sullivan | |
| 6,745,768 B2 | 6/2004 | Colla | |
| 6,752,151 B2 | 6/2004 | Hill | |
| 6,770,037 B2 | 8/2004 | Sullivan | |
| 6,817,361 B2 | 11/2004 | Berthon-Jones et al. | |
| 7,225,809 B1 | 6/2007 | Bowen et al. | |
| 7,296,573 B2 | 11/2007 | Estes | |
| 7,469,698 B1 * | 12/2008 | Childers et al. | 128/204.23 |
| 2002/0036601 A1 | 3/2002 | Puckeridge | |
| 2002/0077856 A1 | 6/2002 | Pawlikowski | |
| 2002/0088464 A1 | 7/2002 | Truschel | |
| 2002/0100477 A1 | 8/2002 | Sullivan | |
| 2002/0162553 A1 | 11/2002 | Hamilton | |
| 2003/0055346 A1 | 3/2003 | Rapoport et al. | |
| 2003/0127097 A1 | 7/2003 | Yurko | |
| 2003/0213488 A1 | 11/2003 | Remmers | |
| 2003/0213489 A1 | 11/2003 | Mechlenburg | |
| 2004/0000310 A1 | 1/2004 | Wickham | |
| 2004/0016433 A1 | 1/2004 | Estes | |
| 2008/0053440 A1 | 3/2008 | Farrugia | |

* cited by examiner

*Primary Examiner* — Steven O Douglas

(57) ABSTRACT

The present invention includes a method and apparatus for the optimized treatment of obstructive sleep apnea. The present invention includes a pressure source configured to provide positive airway pressure to a patient who is resting at home. The pressure source receives control signals from control electronics that define a pressure profile to be delivered to the patient. The control electronics select parameters to define the pressure profile based on factors such as a user selection, information received from a sensor, and/or a prescription.

20 Claims, 13 Drawing Sheets

Fig. 3

PARAMETER OPTIMIZATION IN SLEEP APNEA TREATMENT APPARATUS

RELATED APPLICATIONS

This non-provisional application is a continuation of U.S. Non-Provisional Application Ser. No. 12/271,927 entitled "Parameter Optimization in a Sleep Apnea Treatment Apparatus", filed Nov. 16, 2008 which is a continuation of U.S. Non-Provisional Application Ser. No. 11/224,548 entitled "Parameter Optimization in a Sleep Apnea Treatment Apparatus", filed Sep. 12, 2005. U.S. Non-Provisional Application Ser. No. 11/224,548 claims priority to U.S. Provisional Application Ser. No. 60/609,897, Entitled "Parameter Optimization in a Sleep Apnea Treatment Apparatus" by Winthrop D. Childers and Ruth O. Childers, filed on Sep. 14, 2004, incorporated herein by reference under the benefit of U.S.C. 119 (e).

FIELD OF THE INVENTION

The present invention relates to the treatment of sleep disorders. More particularly, the present invention relates to a method and apparatus for optimizing the treatment of obstructive sleep apnea.

BACKGROUND

OSA (obstructive sleep apnea) is a disease that adversely affects an estimated more than 10 million adults in the United States alone. The disorder manifests itself when a person has repeated trouble breathing at night. The trouble breathing results from a collapse and hence obstruction of the pharynx (throat air passage). When this occurs, at the least it disturbs sleep but can also cause cardiac arrest. Those who suffer from OSA tend to have excessive daytime sleepiness, which can lead to lost productivity and accidents.

The best method for treating OSA is with a device that provides PAP (positive airway pressure) to a patient at night. The patient typically wears a mask such as a mask that fits over the nose. The mask is pressurized with a gas such as air that is maintained a positive gauge pressure that may be in the range of 5 to 25 cm of water. The positive pressure applied to the nose will tend to prevent obstruction by distending the collapsible throat air passage.

The most general form of PAP is CPAP, or continuous positive airway pressure. This is effective, but it can have some drawbacks. For some patients with weakened pulmonary systems, breathing in and out with constant pressure may be labored. For those patients in particular PAP systems that provide variation in pressure that is timed with the cycle of breathing is preferred. This application of pressure is referred to as IPAP (inspiratory positive airway pressure) and EPAP (expiratory positive airway pressure).

Historically OSA has been treated in sleep clinics where the OSA problem can be diagnosed and treated. This tends to be quite expensive, impractical, and uncomfortable. To address these issues, PAP devices have been designed for the home. The devices are relatively inexpensive; in fact, one such device may cost less than spending a few days in a sleep clinic. But along with a great benefit, sending such devices home with patients creates some new issues.

Such issues with take-home PAP systems have to do with patient-to-patient variations and with variations in a particular patient's condition. Historically the proper settings for a PAP device need to be determined in a sleep clinic. This is very expensive and probably impractical given the number of those victimized by OSA. In addition, when a patient has time-based variations this cannot be properly addressed by a sleep clinic. There is a need for a take home PAP apparatus that can address these patient to patient and time based variations.

BRIEF DESCRIPTION OF THE DRAWINGS

FIG. 3 is a schematic block diagram of a PAP (positive airway pressure) treatment apparatus of the present invention.

DETAILED DESCRIPTION OF THE PREFERRED EMBODIMENTS

The present invention is a PAP (positive airway pressure) apparatus configured for use in the home and suitable for treatment of OSA (obstructive sleep apnea). A PAP device of the present invention can be a CPAP (continuous positive airway pressure) device or an IPAP/EPAP (inspiratory positive airway pressure/expiratory positive airway pressure) device. The PAP of the present invention operates or provides "treatment cycles" in multiple modes including a "standard" mode governed by a "standard" set of operating parameters and a "custom" mode governed by a "custom" set of operating parameters. A "treatment cycle" is essentially the complete cycle of "pressure profiles" provided to a patient during a sleep cycle. An example of a "treatment cycle" is discussed with respect to FIG. 9. A "pressure profile" is a pressure versus time applied by the PAP device. Examples of pressure profiles are described with respect to FIGS. 9, 9a, 9b, and 9c.

The PAP apparatus of the present invention includes a mask that is coupled to a controllable pressure source under control of control electronics. The control electronics are coupled to an information storage device and to an input selection device. The information storage device stores information indicative of the operating parameters. From here forward, when we say that the information storage devices "stores" parameters, we mean that the device stores information indicative of the parameters that can be utilized by the control electronics to cause operation of the pressure source that is consistent with the parameters.

The operating parameters include "variable" parameters that can be customized according to the needs of a patient. The information storage device provides storage for redundant values for each of the variable parameters. Thus, for each variable parameter, a "standard version" is stored and one or more "custom versions" are stored. The controller is configured to operate in a "standard" mode when it utilizes a set of standard parameters and to operate in a custom mode when it utilizes a set of custom parameters.

The controller selects an operating mode in response to a mode signal from the input selection device. When the mode signal is received, the controller then loads and/or utilizes a set of parameters for the particular mode selected. The mode may be customized according to the particular patient's intermediate or long term therapeutic needs. Alternatively, the mode may be selected in response to a shorter term transient condition of the patient.

Figure 1:
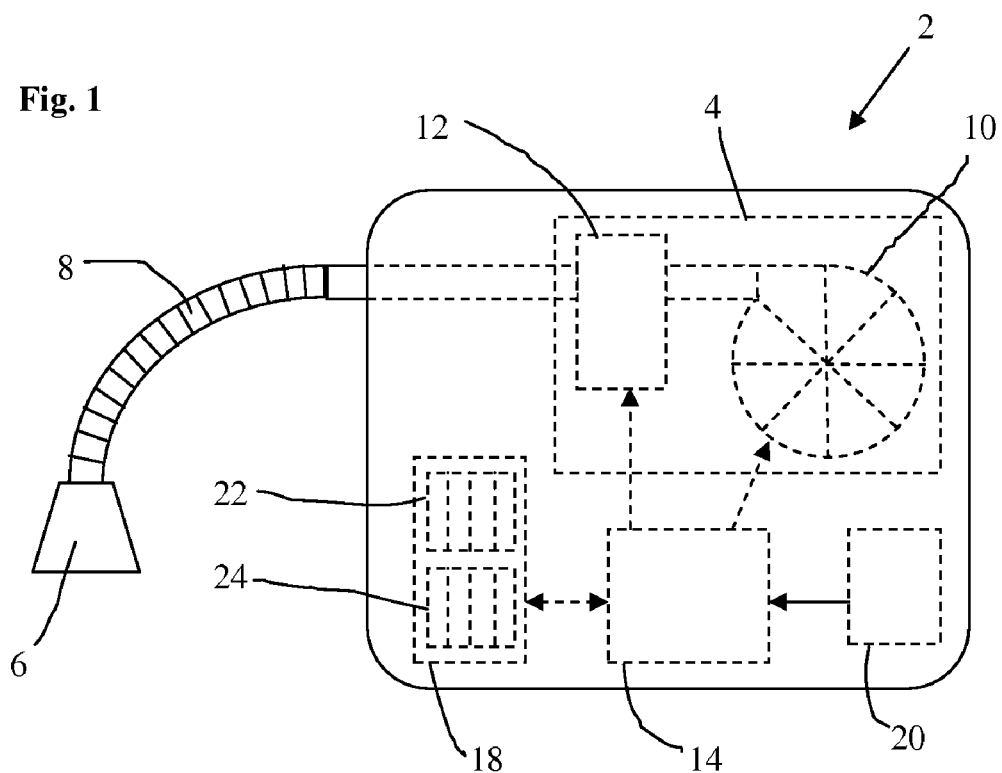
FIG. 1 is a schematic representation of a PAP (positive airway pressure) treatment apparatus of the present invention.
Figure 2:
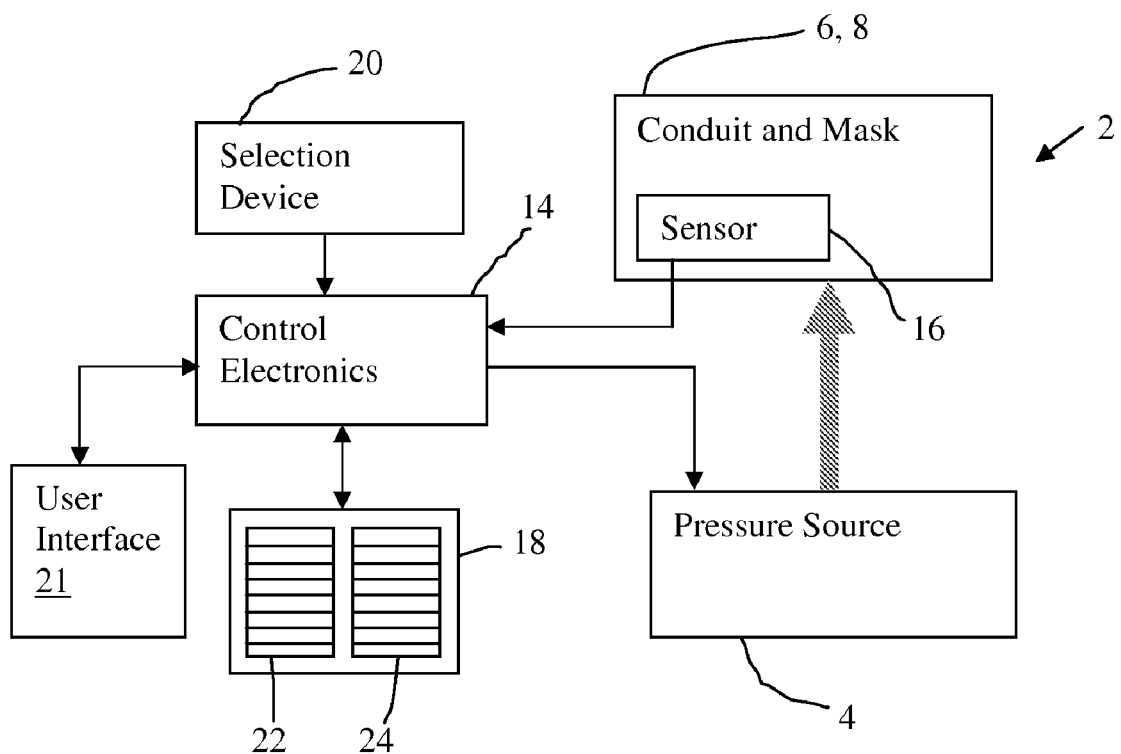
FIG. 2 is a schematic block diagram of a PAP (positive airway pressure) treatment apparatus of the present invention.

A PAP treatment apparatus 2 configured for home based treatment of sleep apnea is depicted schematically in FIG. 1 and in schematic block diagram form in FIG. 2. The treatment apparatus 2 includes a pressure source 4 that is fluidically coupled to a mask 6 via a conduit 8. In one embodiment, the pressure source 4 includes a blower 10 and a pressure modulator 12. During use a patient wears mask 6. PAP treatment apparatus applies positive pressure to the mask via the pressure source 4. In the embodiment wherein the pressure source 4 includes blower 10 and pressure modulator 12, the pressure modulator 12 enhances the speed of response and accuracy of the pressure source 4.

The PAP treatment apparatus 2 includes a controller 14 that is coupled to a sensor 16, an information storage device 18, an input selection device 20, user interface 21, and the pressure source 4. In some embodiments, input selection device is a portion of user interface 21. The controller 14 receives inputs from sensor 16, information storage device 18, input selection device 20, and in provides control signals to pressure source 4.

The information storage device stores information indicative of operating parameters for operating the pressure source 4. The operating parameters include fixed operating parameters that do not vary according to a particular operating mode and variable operating parameters that do vary according to a particular operating mode.

The information storage device stores first or standard operating parameter information 22 and second or custom operating parameter information 24 for each of the variable operating parameters. The standard operating parameter information 22 defines a first or standard operating mode for PAP treatment apparatus 2. The custom operating parameter information 24 defines a second or custom operating mode for PAP treatment apparatus 2.

The controller receives a mode selection from inputs selection device 20 and operates PAP treatment apparatus in a manner consistent with the mode selected. If a first or standard mode is selected, then controller 14 utilizes standard parameters 22. If a second or custom mode is selected, then controller 14 utilizes custom parameters 24.

Figure 3:
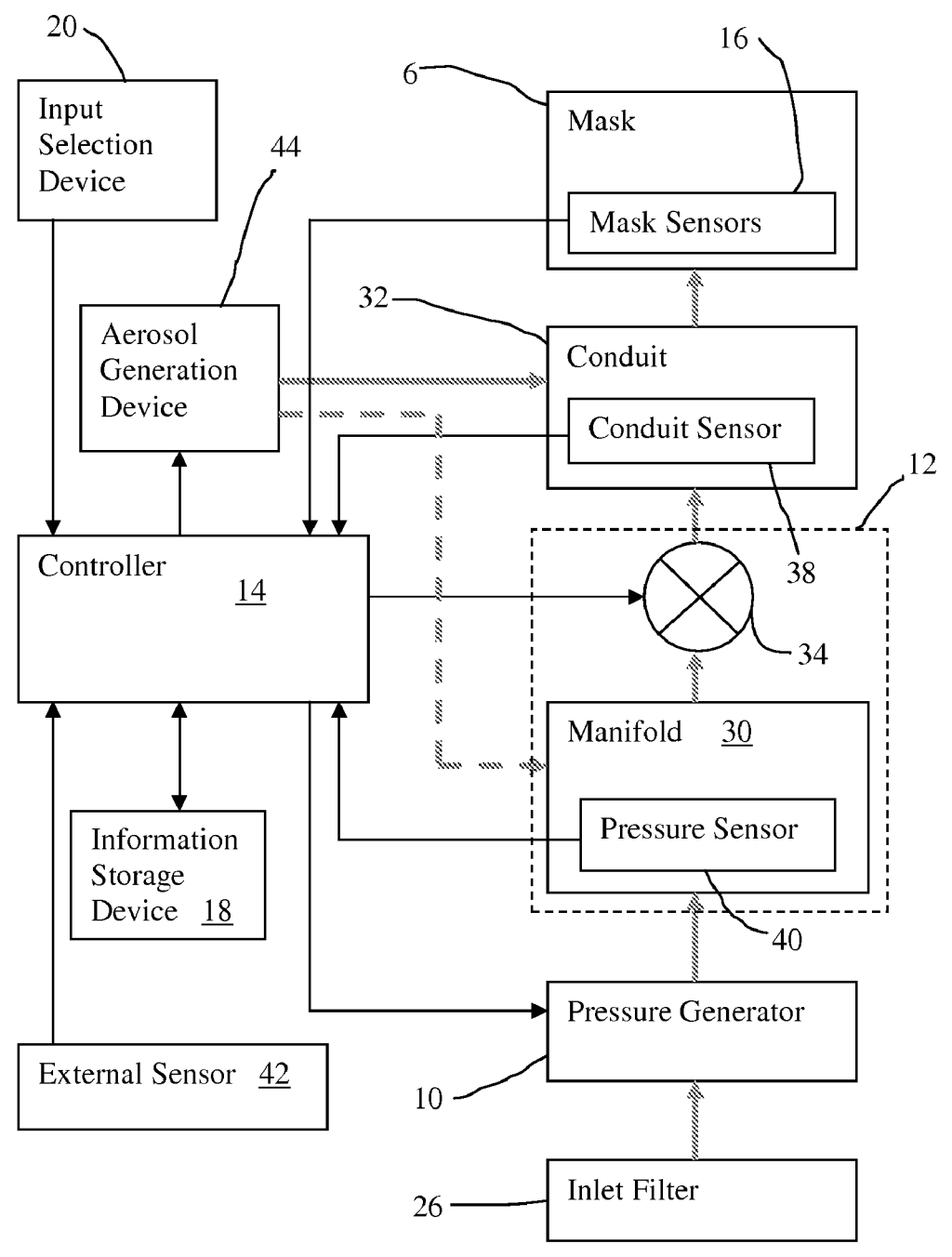

An exemplary PAP treatment apparatus 2 is depicted in more detailed block diagram form in FIG. 3. In the exemplary embodiment, air is received by inlet filter 26 which passes filtered air to an intake of pressure generator 10. Pressure generator 10 supplies pressurized air to an air manifold 30 that "warehouses" pressurized air. Manifold 30 passes air to conduit 32 via valve 34. Together manifold 30 and valve 34 operate together as modulator 12. Finally, conduit 32 provides pressurized air to mask 6 worn by the patient. In this embodiment, the manifold 30 is maintained at a higher gauge pressure than conduit 32 under control of controller 14.

Controller or control electronics 14 is coupled to information storage device 18, input selection device 20, pressure generator 10, valve 34, acoustic sensor or microphone 16, conduit sensor 38, pressure sensor 40, external sensor 42, and aerosol generation device 44. Similar to the embodiment discussed with respect to FIGS. 1 and 2, information storage device 18 stores variable operating parameters that includes a first or standard set of operating parameters and a second or custom set of operating parameters. The controller 14 is configured to receive an instruction from the input selection device 20 and in response to operate pressure generator 10 and pressure modulator 12 using the selected operating parameters.

The input selection device 20 is configured to impart a signal to controller 14 indicative of one or more operating modes for controller 14. An appropriate input selection device can take on any number of forms including a memory card, flash memory, a user selected switch, and LCD touch screen interface, a wireless link, a sensor signal, a "fire-wire" or USB link, an RFID device input, or any other input device that is capable of imparting a signal to controller 14 indicative of an operating mode.

Based upon a mode selected via input selection device 18, controller 14 selects operating parameters that define operation of the PAP treatment device 2 for a treatment cycle. Operating parameters include applied pressure profiles, therapeutic pressure levels, a maximum pressure level, aerosol parameters, and other factors that may be important for a given patient condition. A pressure profile defines a pressure versus time curve to be applied to mask 6. A therapeutic pressure level defines a pressure applied to mask 6 intended to open or prevent obstruction of the throat air passage. A maximum pressure level defines an upper limit for air pressure to be applied to mask 6. Finally aerosol parameters define operating instructions for aerosol generation device 44.

Controller 14 receives signals from one of mask sensors 16 such as a microphone 16 that can be indicative of an obstructive event. Controller 14 also receives information from an external sensor 42 that can be a microphone external to mask 6. Controller 14 can utilize information from the external sensor 42 to subtract our or compensate for noises external to mask 6. Controller 14 utilizes information received input selection device 20, information storage device 18, microphone 16, and external sensor 42 to select a pressure profile applied to mask 6 and to operate aerosol generation device 44.

The pressure profile applied to mask 6 can be rapidly and precisely modulated via a pressure control system that includes pressure generator 10 and pressure modulator 12. Pressure modulator 12 includes manifold 30 and valve 34 under control of controller 14. Controller 14 receives a signal from pressure sensor 40 that is indicative of a manifold pressure level in manifold 30. In the example wherein pressure generator 10 is a fan, the controller 14 adjusts a fan speed to maintain the pressure in manifold 30 within a desired pressure range. Controller 14 receives a signal from a sensor 38 in conduit 8 and/or mask 6 that is indicative of the pressure level in conduit 8. Controller opens and closes valve 34 to maintain a desired pressure range in mask 6. The use of a manifold 30 and valve 34 to regulate pressure in mask 6 allows controller 14 to very precisely and rapidly modulate pressure in mask 6. This is particularly important for IPAP/EPAP systems or where a rapid response to an obstructive event is required. In order for the mask pressure to be properly controlled and for rapid responses, the pressure in manifold 30 is maintained at a level above the anticipated required pressure ranges for mask 6.

Figure 4A:
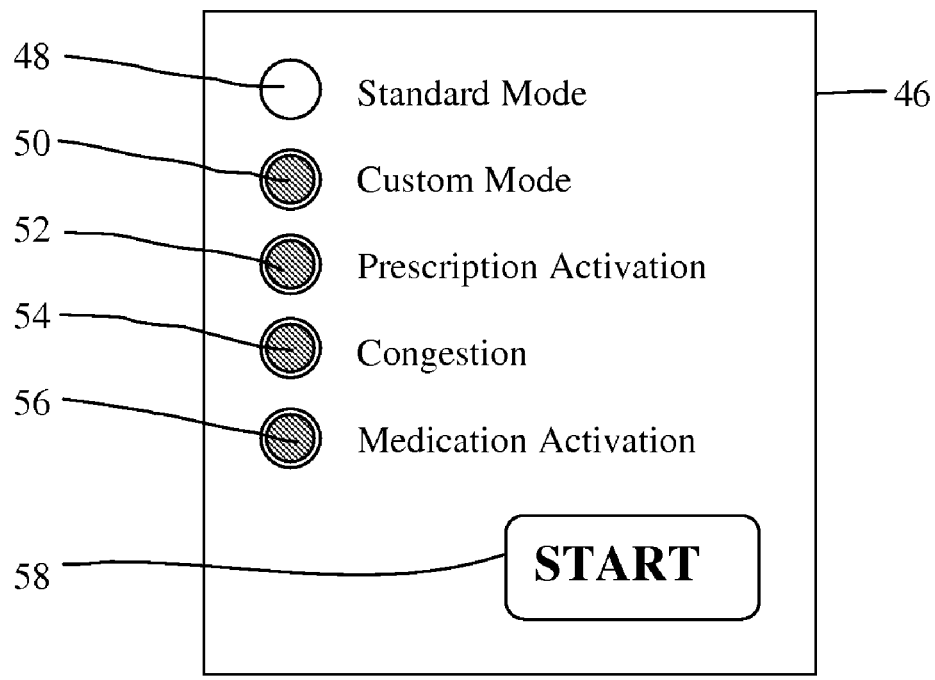
FIG. 4a is an illustration of a portion of a user interface utilized in the PAP (positive airway pressure) treatment apparatus of the present invention for selecting an operating mode.
Figure 4B:
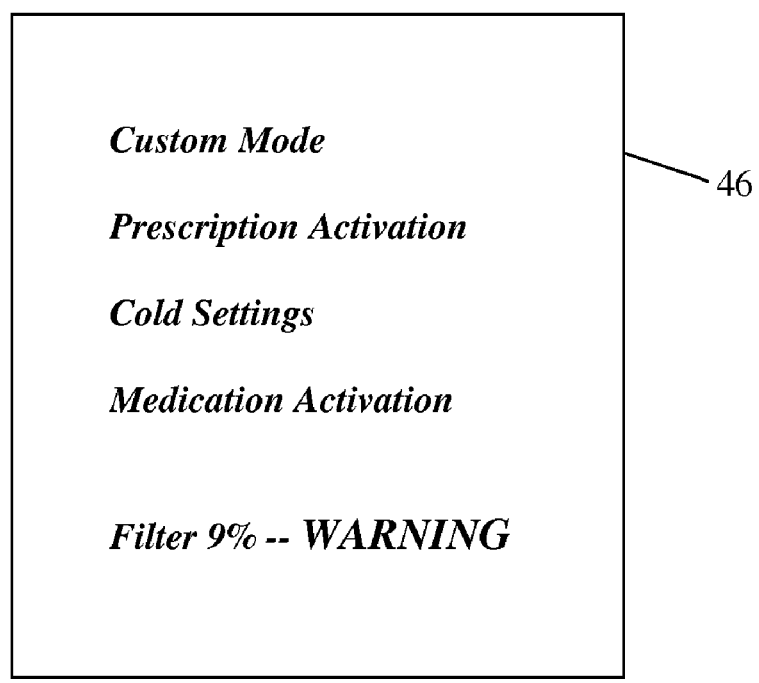
FIG. 4b is an illustration of a portion of a user interface utilized in the PAP (positive airway pressure) treatment apparatus of the present invention during operation.

FIGS. 4a and 4b depict an exemplary user interface 21 for PAP apparatus 2 including a backlit LCD (liquid crystal display) or OLED (organic light emitting diode) touch screen 46. FIG. 4a depicts a view displayed by screen 46 used to select an operating mode for PAP apparatus 2 and FIG. 4b depicts a view displayed by screen 46 during operation. According to FIG. 4a, the operating modes include a standard operating mode that is selected via a top button 48 that would activate the "defaults" for apparatus 2.

By selecting button 50, a "custom" mode can be selected that utilizes operating parameters that have been customized and optimized for the particular patient using PAP apparatus 2. This mode may have one or more particular pressure profiles (defined pressure versus time that is applied to mask 6) that is/are more comfortable or effective for the particular patient.

By selecting button 52, parameters indicative of a prescription may be utilized. For example a prescription may have been provided that allows for a higher maximum therapeutic pressure than the standard operating mode would allow.

By selecting button 54, parameters indicative of a transient condition such as a cold congestion can be utilized. For example, selecting button 54 may activate aerosol device 44 and it may provide a pressure profile that is effective for the particular transient condition.

By selecting button 56, the aerosol device 44 may emit a medicated aerosol. In the illustrated example, buttons 50-56 may be individually selected or all selected at once if there are various customizations and/or transient conditions required for the operation of sleep apnea therapy device 2.

After the "START" 58 button is selected, apparatus 2 begins operating and then displays a screen according to FIG. 4b that indicates selected settings and a condition of filter 26. According to FIG. 4b, the filter has 9% of its expected life remaining and a "WARNING" indicator is displayed to alert the user that the filter is in need of replacement.

Figure 5:
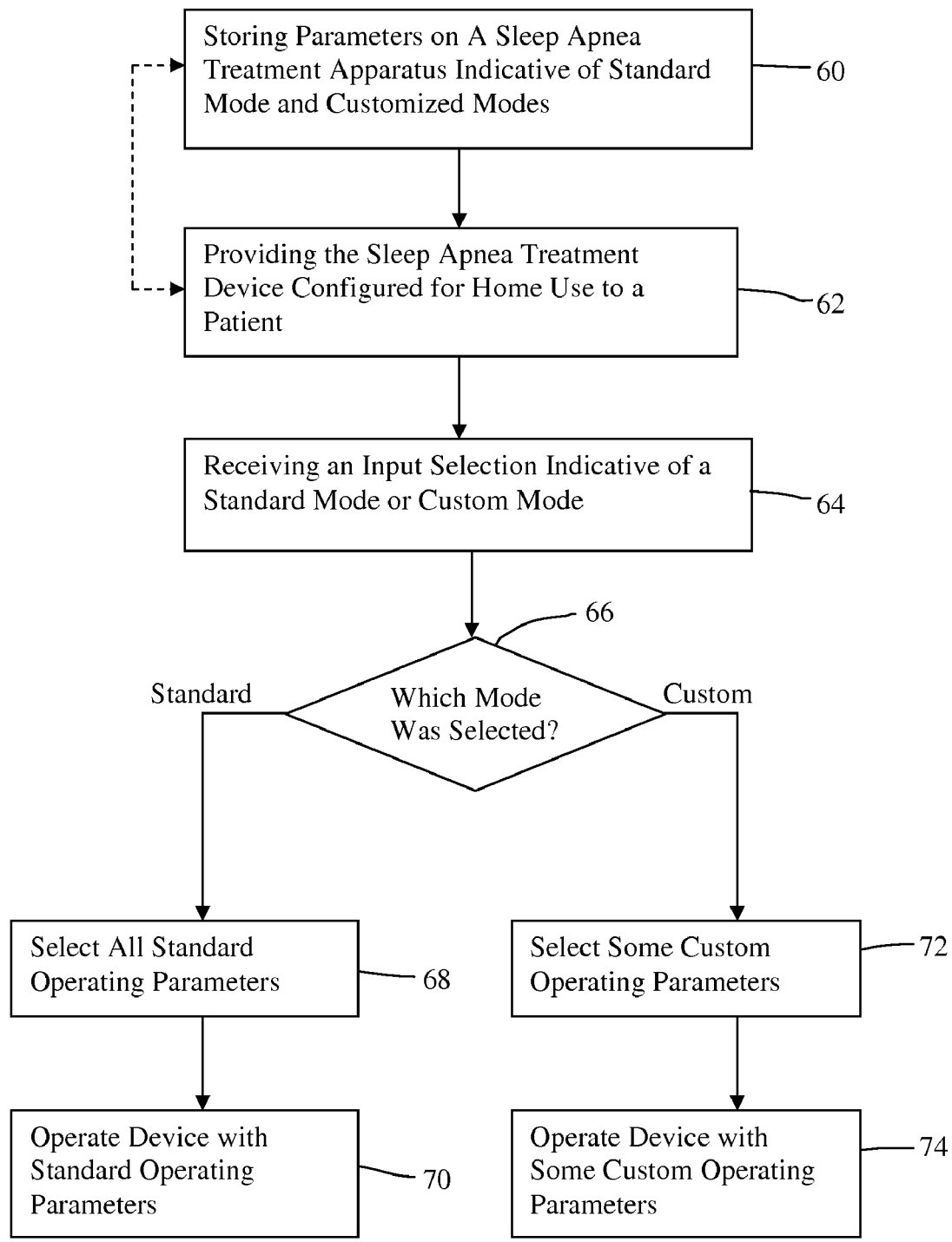
FIG. 5 is a flow chart representation of a method whereby the PAP of the present invention selects between standard and custom operating modes.

An exemplary operation of PAP treatment apparatus is depicted in FIG. 5. According to 60, parameters are stored on information storage device 18 including standard parameters 22 indicative of a "standard" operating mode and custom parameters 24 indicative of a "custom" operating mode. According to 62, the apnea treatment apparatus 2 configured for home use is provided to the patient. In one embodiment, 60 can occur before 62—apparatus 2 can be provided to the patient with the parameters already loaded. Alternatively, 62 can occur before 60.

According to 64, an input selection indicative of a standard operating mode or a custom operating mode is imparted to controller 14 via input selection device 20. According to 66, a decision is made by controller 14 depending upon whether the standard or custom mode is selected. If the standard mode is selected then controller selects standard parameters 22 according to 68 and operates apparatus 2 according to the standard parameters 22 according to 70. If the custom mode is selected, then the controller selects custom parameters 24 according to 72 and operates the apparatus using the custom parameters 24 according to 74.

Figure 6:
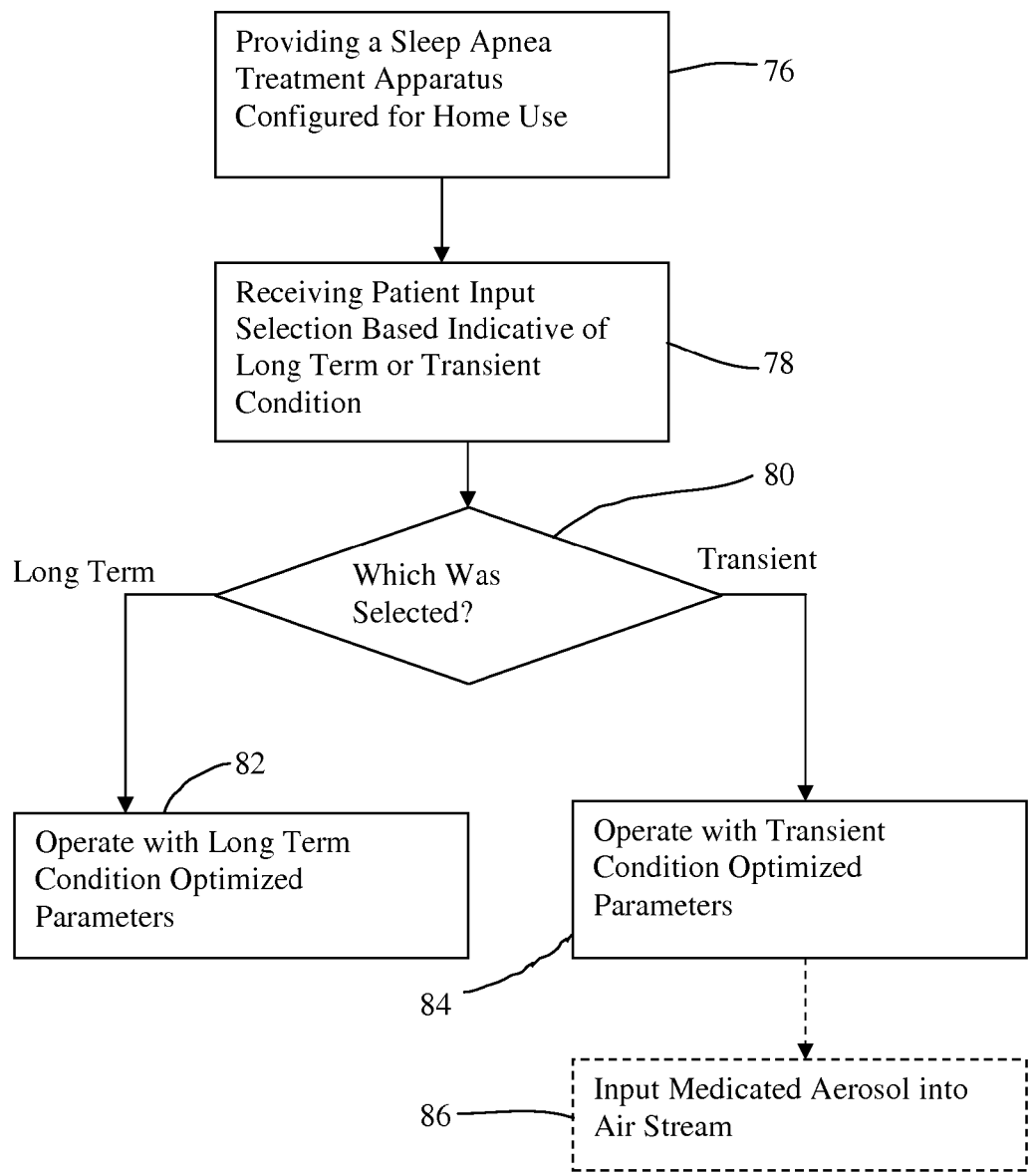
FIG. 6 is a flow chart representation of a method whereby the PAP of the present invention is operated in a way that is optimal either for a long-term condition or a transient condition of a patient.

An exemplary embodiment of the operation of PAP apparatus 2 for treating a transient condition is depicted with respect to FIG. 6. According to 76 a sleep apnea treatment apparatus 2 configured for home use is provided to a patient. According to 78, the patient makes a selection using input selection device 20 to operate the device according to a long-term condition or a transient condition. Stated another way, the user either selects a first operating mode whose variable operating parameters are more optimal for a long-term condition or a second operating mode whose variable operating parameters are more optimal for a transient condition (such as congestion resulting from a viral infection).

A decision 80 is made based on the selection. According to 82, if the long-term or first mode is selected, then treatment apparatus 2 is operated according to long-term optimized parameters. According to 84, if the transient or second operating mode is selected, then apparatus 2 is operated utilizing transient operating mode parameters. These may include, for example, increased breathing assistance pressures or the like for example to offset nasal congestion. According to 86, these parameters may also include inputting medicated aerosol into conduit 8 and hence to mask 6. The medicated aerosol may be generated by aerosol generation device 44.

Figure 7:
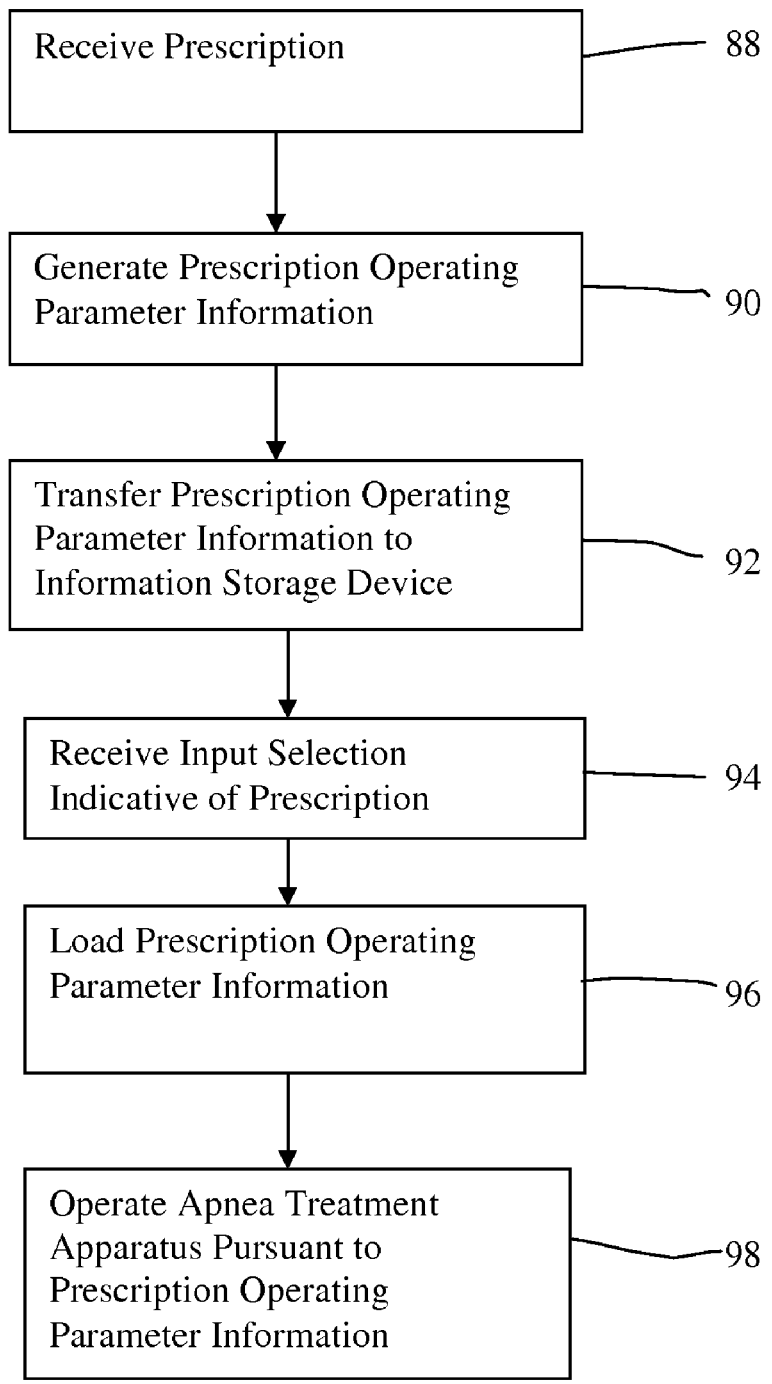
FIG. 7 is a flow chart representation of a method whereby the PAP of the present invention is receives updated operating parameters from a prescription.

Another exemplary embodiment of the operation of PAP apparatus 2 updated by a prescription is depicted with respect to FIG. 7. According to 88, a patient receives a prescription that defines operating parameters for treatment apparatus 2. An example of such an operating parameter might be the maximum operating pressure. This typically will be in the 8-20 cm of water (positive gauge pressure) range in the "default" or standard case. For some patients, the required maximum therapeutic pressure may be greater than 20 cm of water for example.

Other possible parameters by prescription 88 might include: (1) the dispensing of aerosolized medicants for the purpose of clearing a transient congestion problem, or (2) other operational aspects like a time-pressure integral factor. According to 90, the prescription operating parameter information that is usable by apparatus 2 is generated or derived from the prescription.

Then according to 92, the information is transferred to the information storage device 18. This can be done any number of ways. For example, a physician may have a computer for storing prescription or operating parameter information on a flash memory card. Alternatively, the doctor may authorize a separate entity (such a as a service provider) to provide a memory device, an internet transmission, or some other means of providing the proper operating parameters to the information storage device 18.

According to 94, the controller 14 receives an input from selection device that is indicative of the prescription. This could be a user selection from a menu as depicted in FIGS. 4a/b, or it could be the act of plugging in a memory card storing the parameters.

According to 96 and 98, the control electronics then load the prescription operating parameter information and operate treatment apparatus 2 pursuant to the prescription operating parameter information.

Figure 8:
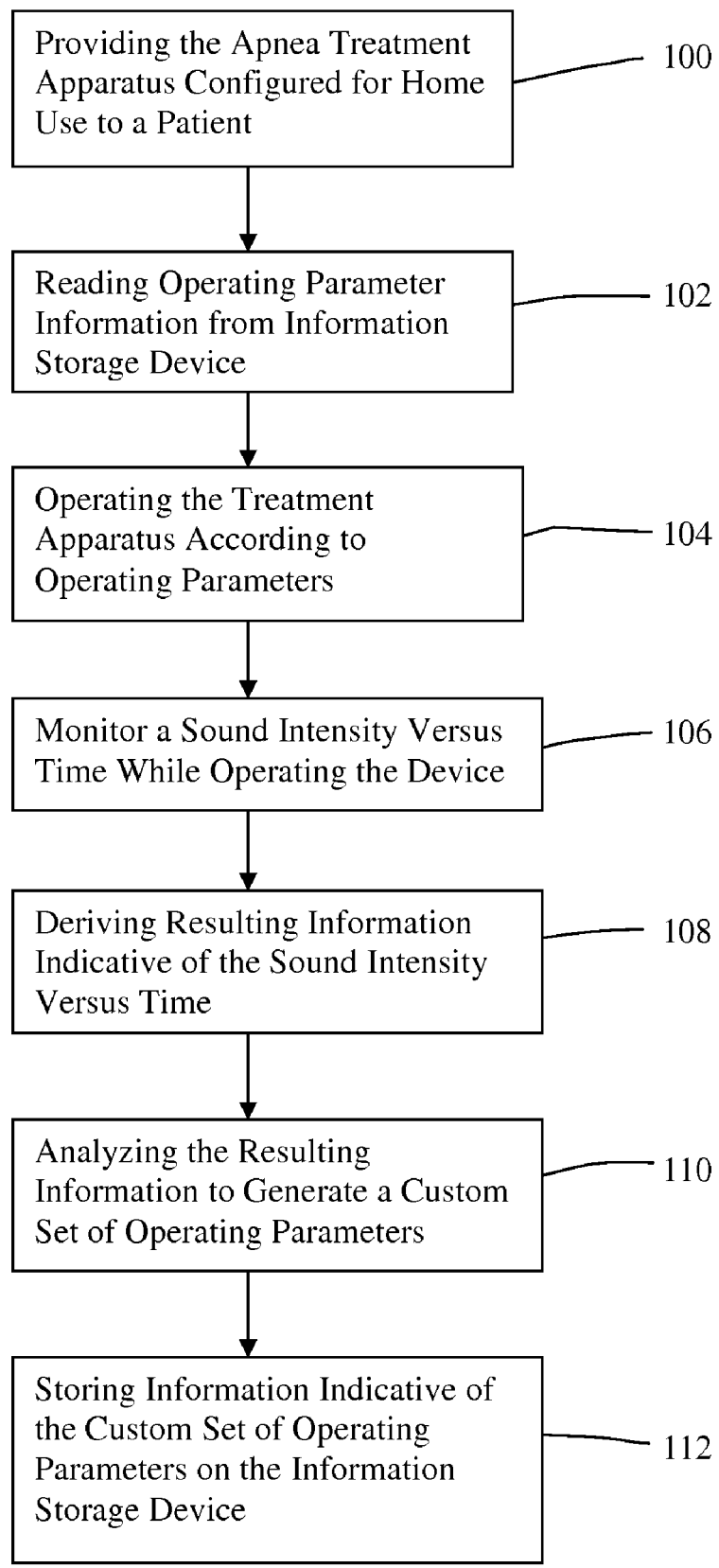
FIG. 8 is a flow chart representation of a method whereby the PAP of the present invention generates new custom operating parameters based on analyzing information based on an acoustic signal monitored in the mask.

An exemplary embodiment of the operation of apnea treatment apparatus is depicted with respect to FIG. 8 wherein the treatment apparatus generates a custom set of operating parameters as a result of analyzing operational results during a treatment. According to 100 an apnea treatment apparatus 2 configured for home use is provided to a patient.

According to 102 and 104, the controller 14 reads operating parameter information parameter information from the information storage device 18 and operates the treatment apparatus applying a pressure versus time to mask 6 pursuant to the operating parameter information read according to 102. According to 106, the controller 14 monitors a signal received from microphone 16 that is indicative of a sound intensity versus time in mask 6. According to 108 the controller then derives resulting information indicative sound intensity versus time.

According to 110, the controller 14 analyzes the resulting information in order to generate or compute a new custom set of operating parameters. According to 112, the new custom set of operating parameters is then stored on the information storage device.

Figure 9:
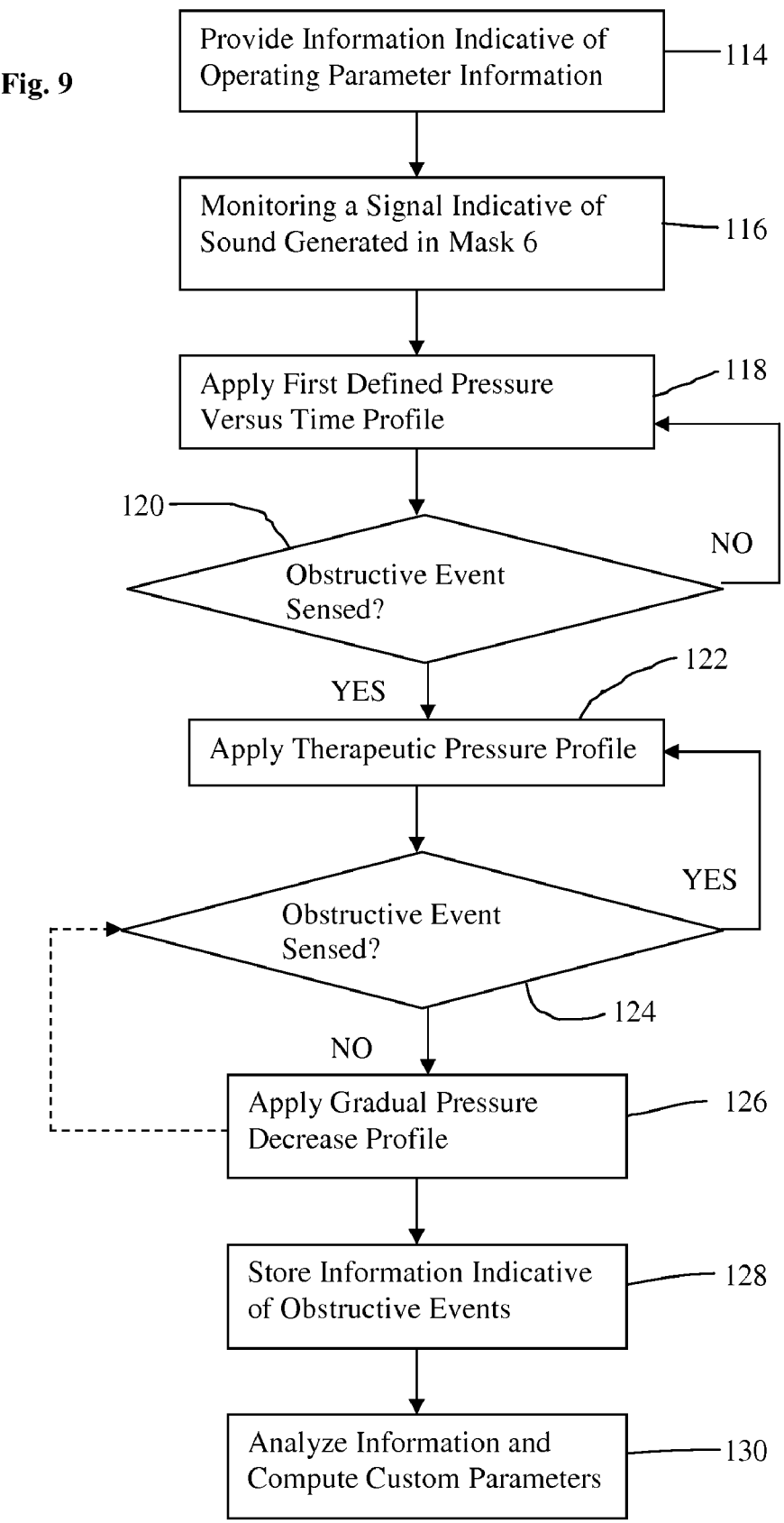
FIG. 9 is a flow chart representation of a method whereby the PAP of the present invention generates new custom operating parameters based on analyzing information based on an acoustic signal monitored in the mask.

A specific treatment cycle that is similar to that depicted with respect to FIG. 8 is now depicted with respect to FIG. 9 in flow chart form. According to 114, operating parameter information is provided from information storage device 18 to controller 14. According to 116 a signal is monitored that is indicative of sounds reaching mask 6. The signal is derived from microphone 16. According to 118, a first or initial pressure profile 118 is applied to mask 6. The first pressure profile is defined by the operating parameters provided according to 114 and is an initial applied pressure versus time profile.

Figure 9A:
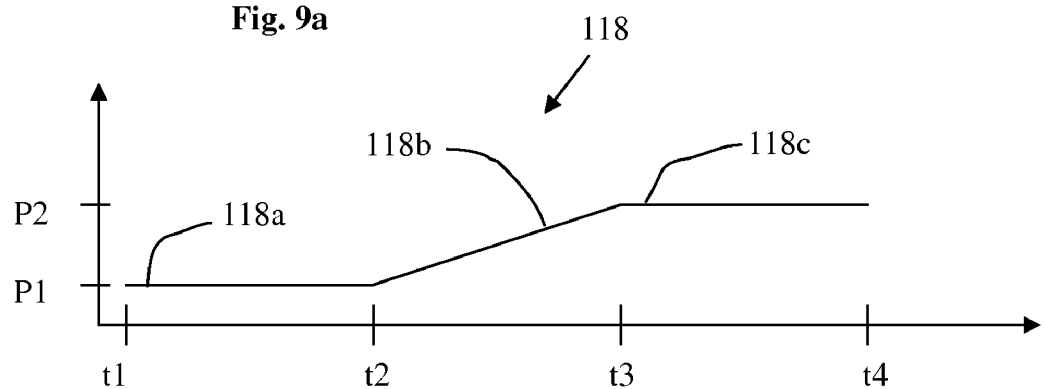
FIG. 9a depicts an initial pressure versus time profile which corresponds to element 118 of FIG. 9.

An exemplary first pressure profile 118 is the initial pressure versus time profile depicted with respect to FIG. 9a. When the patient is first falling asleep, a comfortable first pressure P1 is applied to mask 6 according to portion 118a of profile 118 between times t1 and t2. First pressure P1 may, for example, be in the range of 0 to 4 cm of water positive gauge pressure. After allowing time to fall asleep, the pressure then ramps up according to portion 118b of profile 118 between times t2 and t3. Finally, the pressure level reaches a second pressure P2 that may be in the range of 3 to 8 cm of water for example and this pressure P2 is maintained at a constant level during portion 118c of profile 118. Pressure levels P1 and P1, the slope between time t2 and t3, as well as the time durations of portions 118a, 118b, and 118c are each defined by the parameters provided according to 114 in this example.

Variations are possible as FIG. 9a is for illustrative purposes only. For example pressure versus time curve 118 may be non-linear, or may have multiple flat and sloped portions. The parameters loaded according to 114 define portions of curve 118 individually, or else a single parameter may define the entire curve according to a lookup table. The lookup table in this case would have pressure versus time information for controlling the pressure in mask 6 and a single parameter may select different curves. Also, the magnitude of pressures P1 and P2 may vary markedly depending on the needs of the patient.

According to 120, a decision is made by controller—has a sound indicative of an obstructive event (snoring and/or breathing difficulty) been sensed? If the answer is no, that no event has been sensed, then the profile according to 118 continues. Process 120 may be executed during or after the profile defined by 118 is being executed. If the answer is yes, and an obstructive event is sensed, then a second pressure profile is applied to mask 6 according to 122. The second profile is referred to as an "incident profile" and defines a steep or rapid pressure versus time ramp to aggressively eliminate the obstructive event.

Figure 9B:
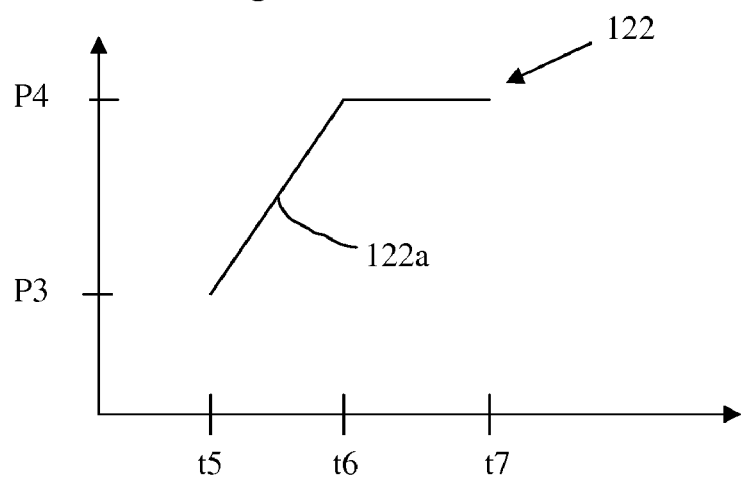
FIG. 9b depicts an incident pressure versus time profile which corresponds to element 122 of FIG. 9.
Figure 9C:
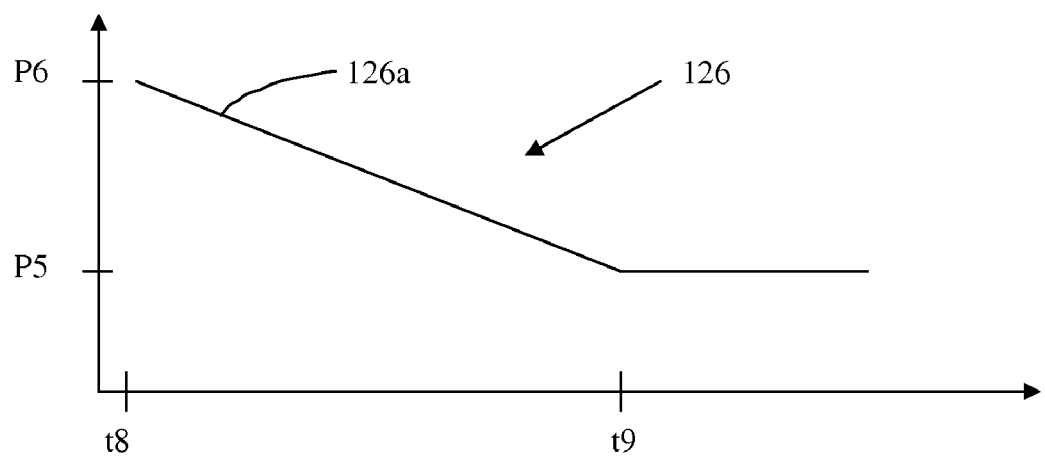
FIG. 9c depicts a third pressure profile which corresponds to element 126 of FIG. 9.

An exemplary embodiment of the second pressure profile 122 is illustrated with respect to FIG. 9b. During a first portion 122a of profile 122, the pressure is rapidly ramping from an initial pressure P3 to a therapeutic pressure P4 while a time progresses from t5 to t6. Pressure P3 may equal pressure P2 in some cases, particularly if first pressure profile 118 has reached pressure P2 before second pressure profile 122 begins. A pressure P4 is reached at time t6. The slope of the pressure ramp defined by portion 122a is defined by the parameters utilized according to step 114. Variations on profile 122 are possible. For example, the ramp may again be non-linear. It may be desirable to have a steeper portion at the beginning of portion 122a to minimize the time required to eliminate the obstructive event. Also, the slope of portion 122a may be determined according to whether the obstructive event is only snoring versus being a dangerous throat obstruction.

While the pressure profile of 122 is being applied, the signal indicative of noise in mask 6 is being monitored. According to 124, a second decision is made. If the obstructive event continues to be sensed, then the second therapeutic profile 122 continues.

If, on the other hand, the obstructive event has stopped (as a result of the therapeutic profile), then a third pressure profile is applied according to 126 wherein the applied pressure is gradually reduced. An exemplary profile 126 is depicted with respect to FIG. 9c. The pressure applied to mask 6 ramps down from a higher pressure P6 to a lower pressure P5 that may be equal to or a little higher than P2 during segment 126a of profile 126. If no more obstructive events are sensed, the pressure be maintained at pressure level P5.

Note that the operating parameters generally define pressure levels P3, P4, P5, and P6. An exception to this would be if a change is sensed before a pressure ramp ends. For example, if according to 124 the obstructive event is no longer sensed before segment 122a is reaches a maximum therapeutic pressure then pressure P4 will be determined by the pressure ramp and the pressure P3 for example. Note that while the flow chart depiction of FIG. 9 has "steps" such as steps 118 and 120, it is to be understand that these steps may overlap in time since sensing a change such as a new obstruction may interrupt the pressure profile of the previous step.

According to 128, information indicative of the obstructive event is stored. According to 130, the information from 128 is analyzed and a new set of custom operating parameters is generated in response. Following are some examples of the new set of custom operating parameters that might be generated.

As a first example, one or more new a parameters may define a new initial pressure profile 118 as applied in step 118. From analyzing the obstructive events, the controller 14 may determine that the initial profile was insufficient to adequately reduce or prevent an obstructive event. Thus, for example the new initial pressure profile would rise to a higher initial operating pressure level P2. As other examples of parametric changes, the time duration of segment 118a may be changed or the slope of segment 118b may be changed.

As a second example, one or more new parameters may define a new incident pressure profile as applied in step 122. From analyzing a continuation of the obstructive events, the controller 14 may determine that the incident pressure profile does not rise aggressively enough to end the obstructive event soon enough. Thus, the slope of segment 122a may be increased and perhaps a peak therapeutic pressure P4 may be increased.

As a third example, one or more new parameters may define a new third pressure profile 126. For example, the final pressure P5 may be increased or decreased.

It is possible that a maximum therapeutic pressure defined by information storage device 18 may not be sufficient to effectively end obstructive events. If that is the case, then step 124 will continue to determine that an obstructive event is occurring event when the highest possible level of pressure P4 (same as the maximum allowed therapeutic pressure) has been reached. In that case therapy device 2 will provide an alarm or other indication that a new prescription is required. An exemplary method for providing such a new prescription is further discussed with respect to FIG. 13.

Figure 10:
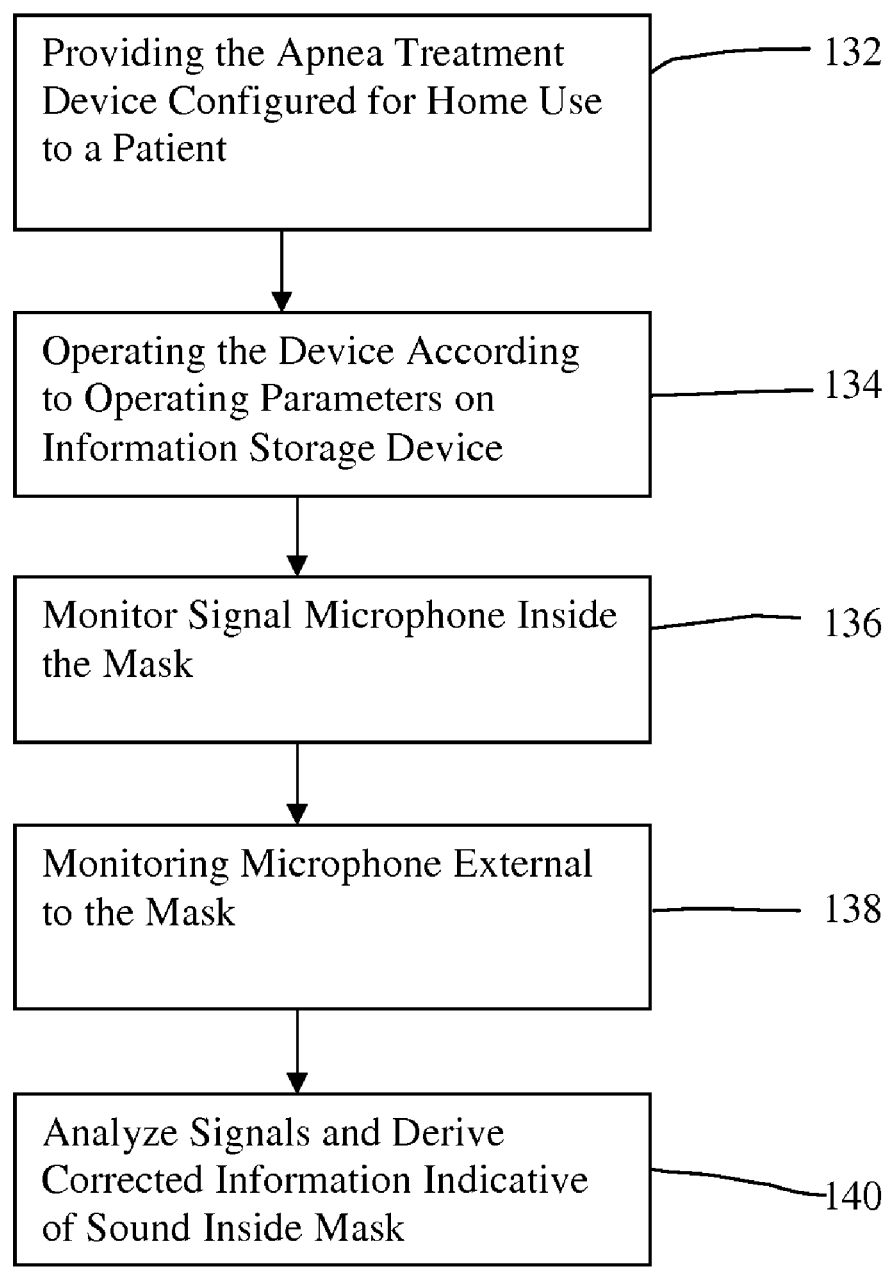
FIG. 10 is a flow chart representation of a method whereby the PAP of the present invention utilizes information from an external sensor to derive a more accurate representation of acoustic noises generated internal to a patient's respiratory system.

An operating method utilizing an external sensor such as a second microphone 42 is depicted with respect to FIG. 10. According to step 132, an apnea treatment apparatus 2 configured for home use is provided to a patient. According to step 134, the apparatus is operated according to operating parameters stored on information storage device 18. According to step 136, a signal from microphone 16 internal to mask 6 is monitored. According to step 138, a signal from microphone 42 external to mask 6 is monitored. According to step 140, the controller 14 analyzes the signals from 136 and 138 and then generates corrected information indicative of sound being generated inside mask 6. This can be used to reduce the effects of noises external to the mask 6 and respiratory system of the patient who is wearing mask 6.

Figure 11:
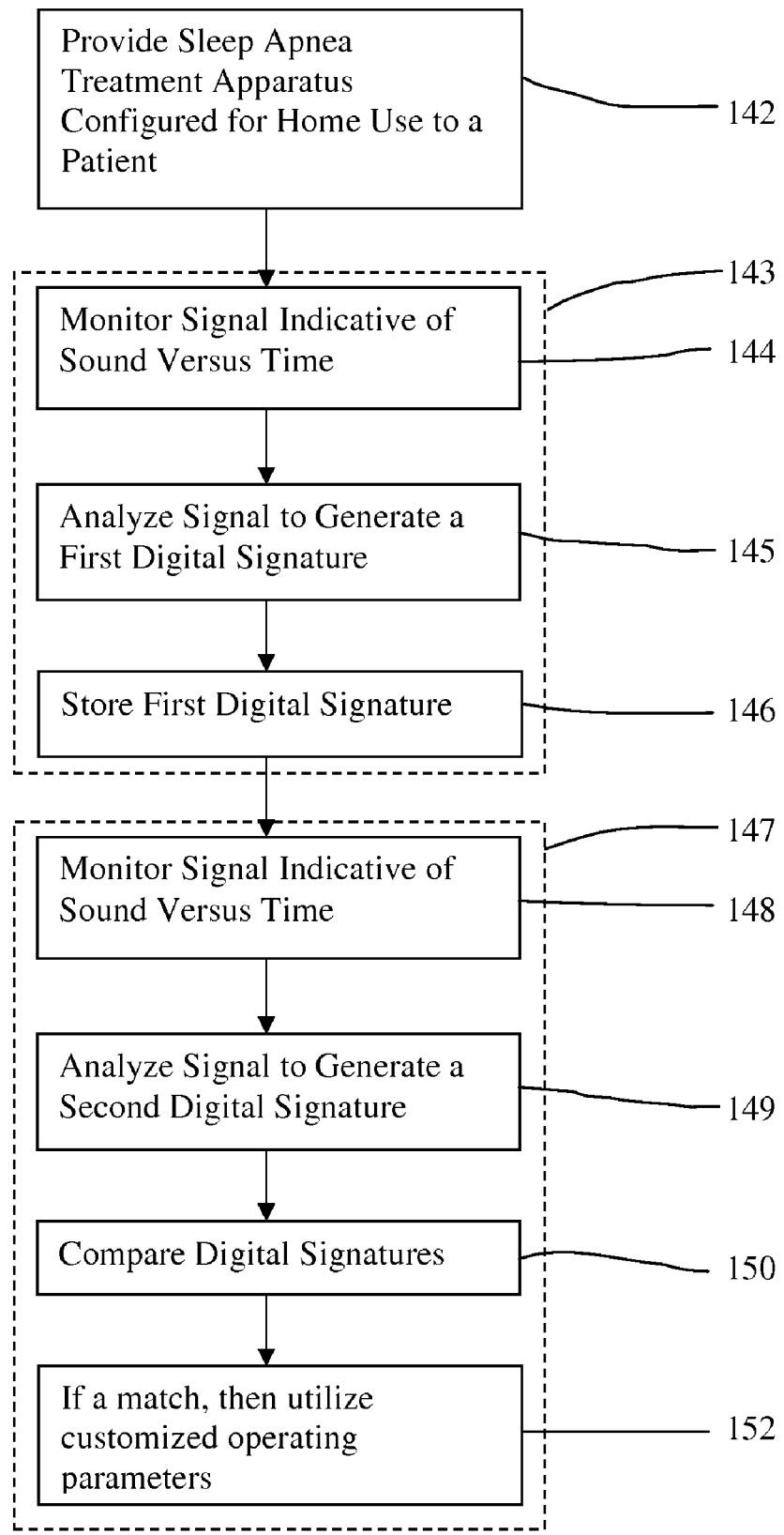
FIG. 11 is a flow chart representation of a method whereby the PAP of the present invention generates and compares a digital signature representation of an acoustic noise pattern over time versus an internally stored digital signature.

An operating method utilizing a digital signature is depicted with respect to FIG. 11. The analysis of waveforms to generate "digital signatures" is known. For example, digital signature methodology is utilized to determine authenticity of signatures by comparing Fourier transforms of the signature curve for example.

According to 142, a sleep apnea treatment apparatus 2 configured for home use is provided to a patient. Sequence 143 includes steps 144-146 and is performed during a first treatment cycle using apparatus 2. According to 144, a signal indicative of a sound in mask 6 versus time is monitored. According to 145, the signal is analyzed to generate a first digital signature. The first digital signature is then stored on information storage device 18 according to 146.

Sequence 147 includes steps 148-152 and is performed during a subsequent second treatment cycle using apparatus 2. According to 148, a second signal indicative of a sound in mask 6 versus time is monitored. According to 149, the second signal is analyzed to generate a second digital signature. According to 150, the first and second digital signatures are compared so as to determine a match. If a match is determined, then customized operating parameters may be utilized to control apparatus 2 according to 152.

The digital signature may be utilized to verify an identity or condition of a particular patient. For example, during step 146, the controller 14 may store information on information storage device indicative of certain operating parameters that are specific to treating a condition implied by the first digital signature.

Figure 12:
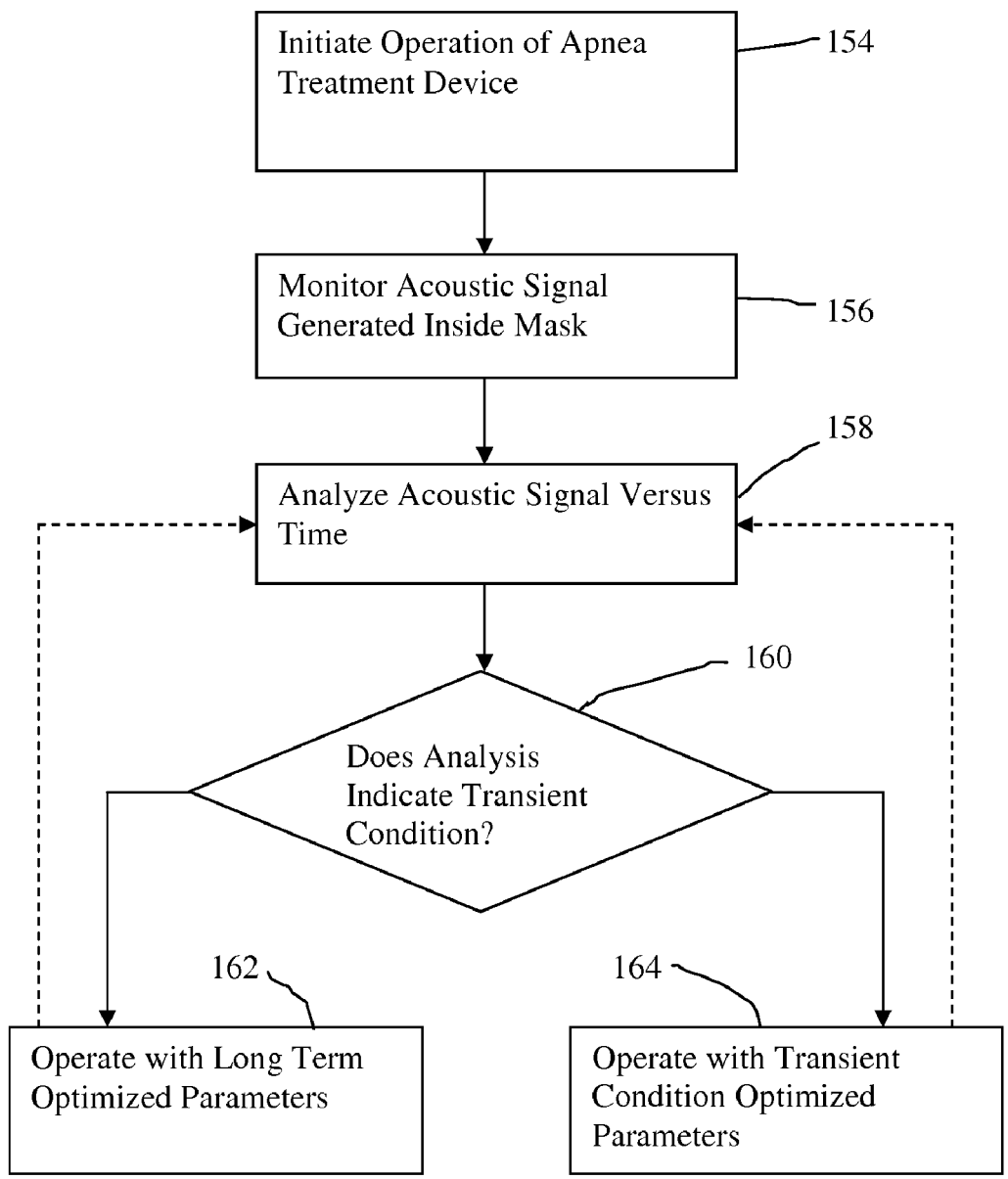
FIG. 12 is a flow chart representation of a method whereby the PAP of the present invention utilizes analysis of sounds inside the mask to determine whether a transient condition is present and to utilize parameters consistent with the determination.

An operating method that is a hybrid between the operating methods of FIGS. 6 and 8 is depicted with respect to FIG. 12. According to 154, PAP treatment device 2 is operated according to operating parameters stored on information storage device 18. According to 156, a signal derived from one or more of sensors 16 or 38 is monitored. According to 158, the signal is analyzed to determine whether characteristics of the signal indicative of a transient condition are present. The controller, in response to this analysis, generates a decision according to 160. If the analysis indicates no transient condition, apparatus 2 is operated using long term optimized operating parameters according to 162. If, however, a transient condition is detected, then the device is operated according to 164 wherein operating parameters optimized for the transient condition are utilized. One clear example of this operation is the case where congestion is detected (as would be evidence with a sounds or pressures indicative of congestion).

As an example of how this might be determined, congestion would tend to reduce a patient's ability to breath through the nose. This could be detected by detecting a reduced breath-imparted flow rate through conduit 8. This would indicate a condition requiring a decongestant and/or an increased flow rate of an aerosol from aerosol generator 44. Thus, 164 would include activating or increasing the activation of aerosol generation device 44.

As another example of 164, the PAP therapy device may provide increased breathing assistance in the event that breathing difficulties are detected.

Figure 13:
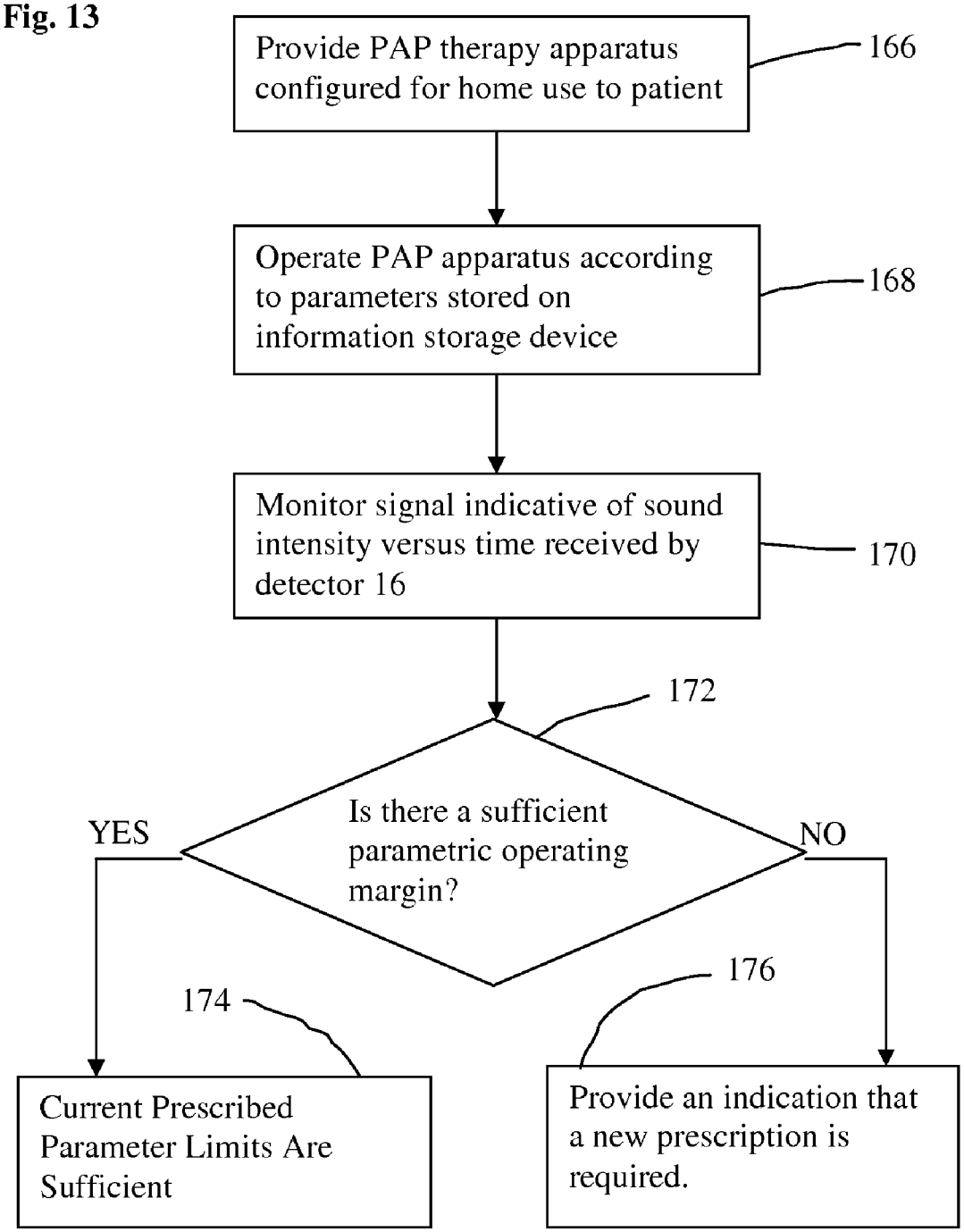
FIG. 13 is a flow chart representation of a method whereby the PAP of the present invention determines whether an insufficient operating margin requires a new prescription.

An operating method for determining if the available pressure range is sufficient is depicted in flow chart form with respect to FIG. 13. According to 166, a PAP therapy apparatus 2 is provided to a patient for home use. According to 168, the therapy apparatus is operated consistent with parameters stored on information storage device 18. The parameters include an upper limit defined for an applied therapeutic pressure level. According to 170, a signal indicative of sound intensity versus time in mask 6 is monitored using sensor 16. As a result of an analysis, a decision is made according to 172—is there a sufficient parametric operating margin?

The parametric operating margin is defined as the difference between the maximum values for the operating parameters and those required to prevent or eliminate obstructive events during operating of treatment apparatus 2. An example of how these parameters are applied is described with respect to FIG. 9. An example of an operating parameter is the maximum pressure level. If the required pressure for treating an obstructive event is close to or exceeds the maximum allowed pressure, then the parametric operating margin is insufficient.

According to 174, if the parametric operating margin is sufficient, then the current prescribed parameter limits (such as maximum pressure level, pressure ramp rates, etc.) are sufficient. If the parametric operating margin is not sufficient, then an indication is provided that a new prescription is required according to 176. This could take the form of an alarm provided to the patient to let the patient know that a prescription is required via user interface 21. In another embodiment, a web-enabled therapy device would directly contact the physician to request an updated prescription.

The method depicted in FIG. 13 can be used in combination with the methods described with respect to FIG. 8 or FIG. 9. Following step 176, the methods of FIG. 7 can then be utilized to provide new prescription control parameters to the information storage device 18.

While various methods have been depicted by flow charts 1-13, it is to be understood that different elements or methods

What we claim is:

1. An apparatus for treating sleep apnea in a patient comprising:
    a pressure source configured to be coupled to a patient airway;
    a sensor configured to monitor the patient airway and generate a signal during a treatment cycle;
    an information storage device configured to store first information representing a first operating mode defining a first pressure profile including an initial pressure profile and an incident pressure profile;
    a controller configured to:
        receive a signal representing the first information;
        operate the pressure source to apply the initial pressure profile before an obstructive event;
        identify an obstructive event based upon analyzing the signal from the sensor;
        operate the pressure source to apply the incident pressure profile in response to the obstructive event;
        generate a new operating mode defining a new pressure profile based upon analyzing the signal from the sensor; and
        store the new operating mode in the information storage device.

2. The apparatus of claim 1 wherein the new pressure profile includes a new initial pressure profile to be applied prior to an obstructive event.

3. The apparatus of claim 1 wherein the new pressure profile includes a new incident pressure profile to be applied during an obstructive event.

4. The apparatus of claim 1 wherein the new pressure profile includes a post-incident pressure profile to be applied following an obstructive event.

5. The apparatus of claim 1 wherein the information storage device is configured to store information representing a plurality of operating modes collectively defining a plurality of different pressure profiles.

6. The apparatus of claim 5 further comprising a user interface configured to receive a selection from a patient of one of the stored operating modes.

7. The apparatus of claim 5 wherein the controller is configured to select one of stored operating modes based upon analyzing the signal from the sensor.

8. The apparatus of claim 5 wherein the stored operating modes include the first operating mode and the new operating mode.

9. The apparatus of claim 1 wherein the sensor is an audio sensor.

10. The apparatus of claim 1 wherein the sensor is responsive to changes in airflow in the patient airway.

11. An apparatus for treating sleep apnea in a patient comprising:
    a pressure source configured to be coupled to a patient airway;
    a sensor configured to monitor the patient airway and generate a signal during a treatment cycle;
    an information storage device configured to store first information representing a first operating mode defining a first pressure profile including an initial pressure profile and an incident pressure profile;
    a controller configured to:
        during a first treatment cycle:
            receive a signal representing the first information;
            operate the pressure source to apply the initial pressure profile before an obstructive event;
            identify an obstructive event based upon analyzing the signal from the sensor;
            operate the pressure source to apply the incident pressure profile in response to the obstructive event;
            generate a new operating mode defining a new pressure profile based upon analyzing the signal from the sensor during the first treatment cycle;
            store second information representing the new operating mode;
        during a second treatment cycle:
            receive a signal representing the second information; and
            operate the pressure source to apply the new pressure profile.

12. The apparatus of claim 11 wherein the new pressure profile includes a new initial pressure profile, and the controller is configured to operate the pressure source to apply the new initial pressure profile before an obstructive event during the second treatment cycle.

13. The apparatus of claim 11 wherein the new pressure profile includes a new incident pressure profile, and the controller is configured to operate the pressure source to apply the new incident pressure profile upon detection of an obstructive event during the second treatment cycle.

14. The apparatus of claim 11 wherein the new pressure profile includes a post-incident pressure profile to be applied following an obstructive event.

15. The apparatus of claim 11 wherein the controller is configured to generate an alarm if the new pressure profile is not sufficient to mitigate apnea events for the patient.

16. An apparatus for treating sleep apnea in a patient comprising:
    a pressure source configured to be coupled to a patient airway;
    a sensor configured to monitor the patient airway and generate a signal during a treatment cycle;
    an information storage device configured to store first information representing a first operating mode defining a first pressure profile including an initial pressure profile and an incident pressure profile;
    a controller configured to:
        receive a signal representing the first information;
        operate the pressure source to apply the initial pressure profile before an obstructive event;
        identify an obstructive event based upon analyzing the signal from the sensor;
        operate the pressure source to apply the incident pressure profile in response to the obstructive event;
        determine whether the first operating mode is sufficient to mitigate obstructive events based on analyzing the signal from the sensor;
        generate a new operating mode defining a new pressure profile if the first operating mode is not sufficient; and
        store the new operating mode in the information storage device.

17. The apparatus of claim 16 wherein the new pressure profile includes a new initial pressure profile to be applied prior to an obstructive event.

18. The apparatus of claim 16 wherein the new pressure profile includes a new incident pressure profile to be applied during an obstructive event.

19. The apparatus of claim 16 wherein the new pressure profile includes a post-incident pressure profile to be applied following an obstructive event.

20. The apparatus of claim 16 wherein the controller is configured to generate an alarm if the new pressure profile is not sufficient to mitigate apnea events for the patient.

* * * * *